United States Patent
Perkins et al.

(10) Patent No.: US 8,911,490 B2
(45) Date of Patent: Dec. 16, 2014

(54) INTEGRATED MESH HIGH METAL TO VESSEL RATIO STENT AND METHOD

(75) Inventors: Keith Perkins, Santa Rosa, CA (US);
Samuel Robaina, Santa Rosa, CA (US);
Jeffery Argentine, Petaluma, CA (US);
Walter Bruszewski, Windsor, CA (US);
Andrew Kiehl, Santa Rosa, CA (US)

(73) Assignee: Medtronic Vascular, Inc., Santa Rosa, CA (US)

( * ) Notice: Subject to any disclaimer, the term of this patent is extended or adjusted under 35 U.S.C. 154(b) by 322 days.

(21) Appl. No.: 13/431,732

(22) Filed: Mar. 27, 2012

(65) Prior Publication Data
US 2013/0261732 A1  Oct. 3, 2013

Related U.S. Application Data

(63) Continuation-in-part of application No. 13/430,942, filed on Mar. 27, 2012.

(51) Int. Cl.
*A61F 2/82* (2013.01)

(52) U.S. Cl.
USPC ........................................ 623/1.15

(58) Field of Classification Search
USPC .............................. 623/1.11–1.48
See application file for complete search history.

(56) References Cited

U.S. PATENT DOCUMENTS

| | | |
|---|---|---|
| 5,800,526 A | 9/1998 | Anderson et al. |
| 5,817,126 A | 10/1998 | Imran |
| 5,817,152 A | 10/1998 | Birdsall et al. |
| 6,093,199 A | 7/2000 | Brown et al. |
| 6,152,956 A | 11/2000 | Pierce |
| 6,190,402 B1 | 2/2001 | Horton et al. |
| 6,270,524 B1 | 8/2001 | Kim |
| 6,344,052 B1 | 2/2002 | Greenan et al. |
| 6,451,051 B2 | 9/2002 | Drasler et al. |
| 7,069,835 B2 | 7/2006 | Nishri et al. |
| 7,093,527 B2 | 8/2006 | Rapaport et al. |
| 7,275,471 B2 | 10/2007 | Nishri et al. |
| 7,306,624 B2 | 12/2007 | Yodfat et al. |
| 7,331,987 B1 | 2/2008 | Cox |
| 7,416,558 B2 * | 8/2008 | Yip et al. ............... 623/1.15 |

(Continued)

FOREIGN PATENT DOCUMENTS

| | | |
|---|---|---|
| EP | 1302179 | 4/2003 |
| EP | 1621159 | 2/2006 |

(Continued)

OTHER PUBLICATIONS

Kallmes, et al., "A New Endoluminal, Flow-Disrupting Device for Treatment of Saccular Aneurysms" Stroke, pp. 2346-2352, Aug. 2007.

(Continued)

*Primary Examiner* — Suzette J Gherbi (57) ABSTRACT

A method includes covering ostai of branch vessels emanating from a main vessel and an aneurysm with an integrated mesh high metal to vessel ratio stent. The integrated mesh high metal to vessel ratio stent includes serpentine rings integrated with an integrated mesh having holes formed therein. A metal to vessel ratio of the integrated mesh high metal to vessel ratio stent is sufficiently high to encourage tissue ingrowth around the integrated mesh high metal to vessel ratio stent yet is sufficiently low to ensure perfusion of the branch vessels through the integrated mesh high metal to vessel ratio stent.

14 Claims, 10 Drawing Sheets

(56) References Cited

U.S. PATENT DOCUMENTS

| | | | |
|---|---|---|---|
| 7,572,290 B2 | 8/2009 | Yodfat et al. | |
| 7,588,597 B2 | 9/2009 | Frid | |
| 7,828,834 B2 | 11/2010 | Garbe | |
| 2002/0013616 A1 | 1/2002 | Carter et al. | |
| 2002/0138133 A1* | 9/2002 | Lenz et al. | 623/1.15 |
| 2003/0109917 A1 | 6/2003 | Rudin et al. | |
| 2003/0130720 A1 | 7/2003 | DePalma et al. | |
| 2003/0204244 A1* | 10/2003 | Stiger | 623/1.16 |
| 2004/0215312 A1 | 10/2004 | Andreas | |
| 2004/0267352 A1 | 12/2004 | Davidson et al. | |
| 2005/0131524 A1 | 6/2005 | Majercak | |
| 2005/0177224 A1 | 8/2005 | Fogarty et al. | |
| 2007/0010872 A1 | 1/2007 | Gregorich | |
| 2007/0168018 A1 | 7/2007 | Amplatz et al. | |
| 2007/0265695 A1 | 11/2007 | Majercak | |
| 2008/0033522 A1* | 2/2008 | Grewe et al. | 623/1.11 |
| 2008/0208319 A1* | 8/2008 | Rabkin et al. | 623/1.16 |
| 2008/0249597 A1* | 10/2008 | Russell et al. | 623/1.2 |
| 2009/0054966 A1* | 2/2009 | Rudakov et al. | 623/1.15 |
| 2009/0138070 A1* | 5/2009 | Holzer et al. | 623/1.15 |
| 2009/0187240 A1* | 7/2009 | Clerc et al. | 623/1.17 |
| 2009/0234429 A1 | 9/2009 | Lau | |
| 2009/0248131 A1* | 10/2009 | Greenan | 623/1.13 |
| 2009/0259292 A1 | 10/2009 | Bonhoeffer | |
| 2009/0270970 A1 | 10/2009 | Yodfat et al. | |
| 2010/0174358 A1* | 7/2010 | Rabkin et al. | 623/1.16 |
| 2010/0184507 A1 | 7/2010 | Gatto et al. | |
| 2010/0198334 A1 | 8/2010 | Yodfat et al. | |
| 2010/0262217 A1 | 10/2010 | Bruszewski | |
| 2010/0274345 A1 | 10/2010 | Rust | |
| 2011/0040367 A1* | 2/2011 | Vinluan | 623/1.13 |
| 2011/0137407 A1 | 6/2011 | Nguyen et al. | |
| 2012/0022508 A1 | 1/2012 | Gross et al. | |
| 2012/0165917 A1* | 6/2012 | Schreck et al. | 623/1.13 |
| 2012/0271399 A1 | 10/2012 | Perkins et al. | |
| 2012/0271407 A1* | 10/2012 | Jones et al. | 623/1.16 |
| 2012/0323307 A1* | 12/2012 | Richter | 623/1.16 |
| 2013/0131780 A1* | 5/2013 | Armstrong et al. | 623/1.13 |
| 2013/0197624 A1* | 8/2013 | Armstrong et al. | 623/1.18 |
| 2013/0261727 A1* | 10/2013 | Perkins et al. | 623/1.12 |
| 2013/0261728 A1* | 10/2013 | Perkins et al. | 623/1.12 |

FOREIGN PATENT DOCUMENTS

| | | |
|---|---|---|
| EP | 1652495 | 5/2006 |
| WO | 98/47447 A1 | 10/1998 |
| WO | WO98/47447 | 10/1998 |
| WO | 03/007840 A2 | 1/2003 |
| WO | WO03/007840 | 1/2003 |
| WO | WO2006/124824 | 11/2006 |
| WO | WO 2008/051554 | 5/2008 |
| WO | WO 2008/091515 | 7/2008 |
| WO | WO2009/137296 | 11/2009 |
| WO | WO2011/008989 | 1/2011 |
| WO | WO2011/012147 | 2/2011 |

OTHER PUBLICATIONS

Fiorella et al., "Definitive Reconstruction of Circumferential, Fusiform Intracranial Aneurysms With the Pipeline Embolization Device" neurosurgery, vol. 62, No. 5, May 2008, pp. 1115-1121.

Fiorella et al., "Curative Reconstruction of a giant Midbasilar Trunk Aneurysm with the Pipeline Embolization Device" Neurosurgery, vol. 64, No. 2, Feb. 2009, pp. 212-217.

* cited by examiner

INTEGRATED MESH HIGH METAL TO VESSEL RATIO STENT AND METHOD

CROSS-REFERENCE TO RELATED APPLICATIONS

This application claims the benefit and priority of U.S. application Ser. No. 13/430,942 filed Mar. 27, 2012, entitled "High Metal to Vessel Ratio Stent and Method" and is herein incorporated by reference for all purposes.

BACKGROUND

The present application relates to an intra-vascular device and method. More particularly, the present application relates to a device for treatment of intra-vascular diseases.

DESCRIPTION OF THE RELATED ART

A conventional stent-graft typically includes a radially expandable reinforcement structure, formed from a plurality of annular stent rings, and a cylindrically shaped layer of graft material, sometimes called graft cloth, defining a lumen to which the stent rings are coupled. Main stent-grafts are well known for use in tubular shaped human vessels.

To illustrate, endovascular aneurysmal exclusion is a method of using a stent-graft to exclude pressurized fluid flow from the interior of an aneurysm, thereby reducing the risk of rupture of the aneurysm and the associated invasive surgical intervention.

Stent-grafts with custom side openings are sometimes fabricated to accommodate the particular vessel structure of each individual patient. Specifically, as the location of branch vessels emanating from a main vessel, e.g., having the aneurysm, varies from patient to patient, stent-grafts are fabricated with side openings customized to match the position of the branch vessels of the particular patient. However, custom fabrication of stent-grafts is relatively expensive and time consuming.

Further, the stent-grafts must be deployed such that the custom side openings are precisely aligned with the respective locations of the branch vessels. This is a relatively complex procedure thus increasing the risk of the procedure.

SUMMARY

A method includes covering ostai of branch vessels emanating from a main vessel and an aneurysm with an integrated mesh high metal to vessel ratio stent. The integrated mesh high metal to vessel ratio stent includes serpentine rings integrated with an integrated mesh having holes formed therein.

A metal to vessel ratio of the integrated mesh high metal to vessel ratio stent is sufficiently high to encourage tissue ingrowth around the integrated mesh high metal to vessel ratio stent yet is sufficiently low to ensure perfusion of the branch vessels through the integrated mesh high metal to vessel ratio stent. The ingrowth of tissue provides secure fixation and sealing of the integrated mesh high metal to vessel ratio stent to the main vessel (tissue remodeling) and essentially eliminates the aneurysm from the main vessel circulation. Further, as the entire integrated mesh high metal to vessel ratio stent is permeable, the integrated mesh high metal to vessel ratio stent is deployed without having to rotationally position the integrated mesh high metal to vessel ratio stent to allow for the perfusion of the target branch vessels as is currently done with branched and fenestrated devices.

These and other features of embodiments will be more readily apparent from the detailed description set forth below taken in conjunction with the accompanying drawings.

BRIEF DESCRIPTION OF THE DRAWINGS

In the following description, the same or similar elements are labeled with the same or similar reference numbers.

DETAILED DESCRIPTION

Figure 16:
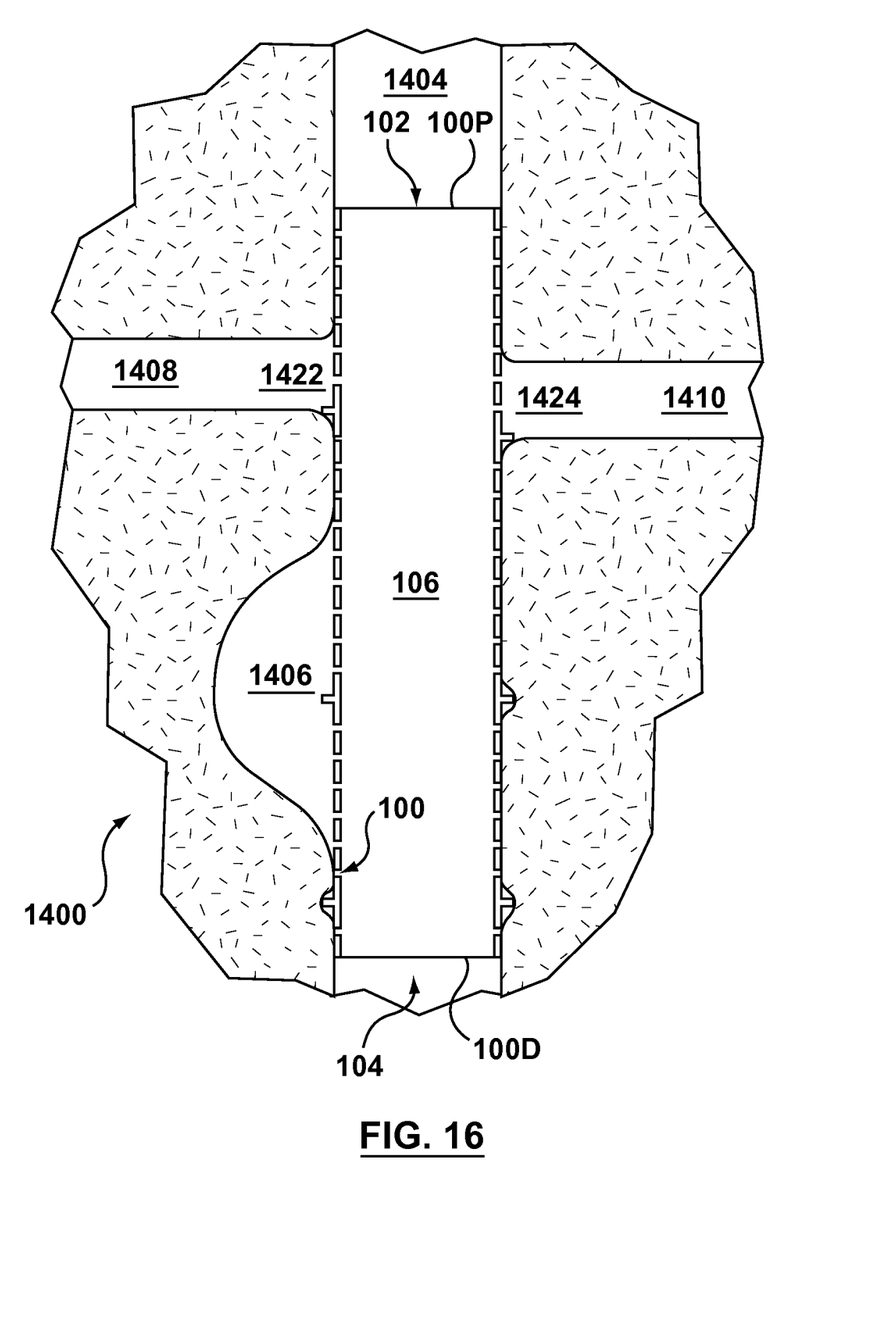
FIG. 16 is a cross-sectional view of the vessel assembly of FIGS. 14-15 after deployment of the integrated mesh high metal to vessel ratio stent of FIGS. 1 and 2 in accordance with one embodiment.

As an overview and in accordance with one embodiment, referring to FIG. 16, a method includes covering ostai 1422, 1424 of branch vessels 1408, 1410 emanating from a main vessel 1404 with an integrated mesh high metal to vessel ratio stent 100. A metal to vessel ratio of integrated mesh high metal to vessel ratio stent 100 is sufficiently high to encourage tissue ingrowth around integrated mesh high metal to vessel ratio stent 100 yet is sufficiently low to ensure perfusion of branch vessels 1408, 1410 through integrated mesh high metal to vessel ratio stent 100. The ingrowth of tissue provides secure fixation and sealing of integrated mesh high metal to vessel ratio stent 100 to main vessel 1404 thus minimizing the risk of endoleaks and migration.

Further, deployment of integrated mesh high metal to vessel ratio stent 100 is relatively simple thus minimizing the complexity and thus risk of deploying integrated mesh high metal to vessel ratio stent 100. More particularly, as the entire integrated mesh high metal to vessel ratio stent 100 is permeable, integrated mesh high metal to vessel ratio stent 100 is deployed without having to rotationally position integrated mesh high metal to vessel ratio stent 100 to be aligned with branch vessels 1408, 1410 as is currently done with deployment of branched and fenestrated devices.

Figure 17:
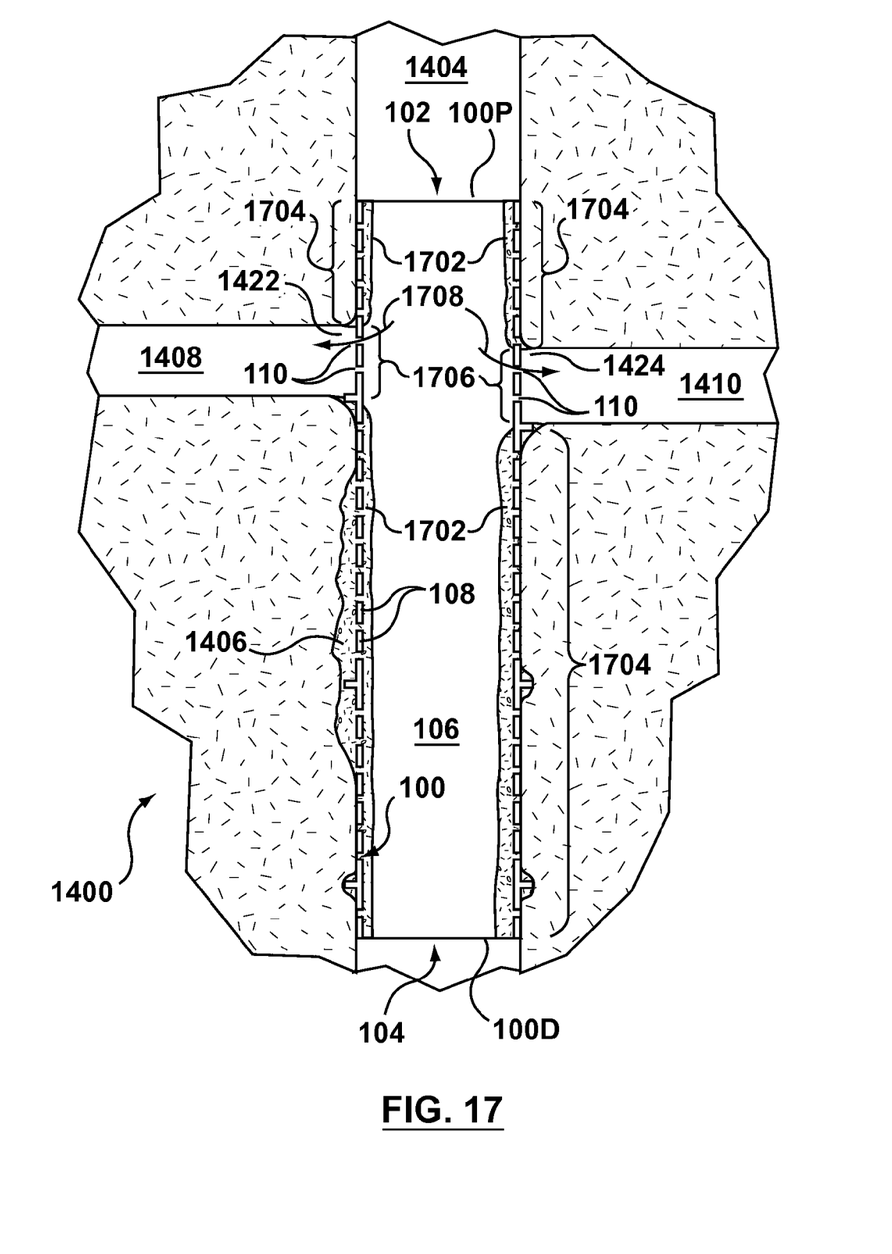
FIG. 17 is a cross-sectional view of the vessel assembly of FIG. 16 illustrating tissue ingrowth into the integrated mesh high metal to vessel ratio stent.

The method further includes covering and excluding an aneurysm 1406 of main vessel 1404 with integrated mesh high metal to vessel ratio stent 100. Referring now to FIGS. 16 and 17 together, the ingrowth of tissue 1702 restricts expansion of aneurysm 1406. In one embodiment, aneurysm 1406 is remodeled and essentially eliminated as illustrated in FIG. 17.

Figure 1:
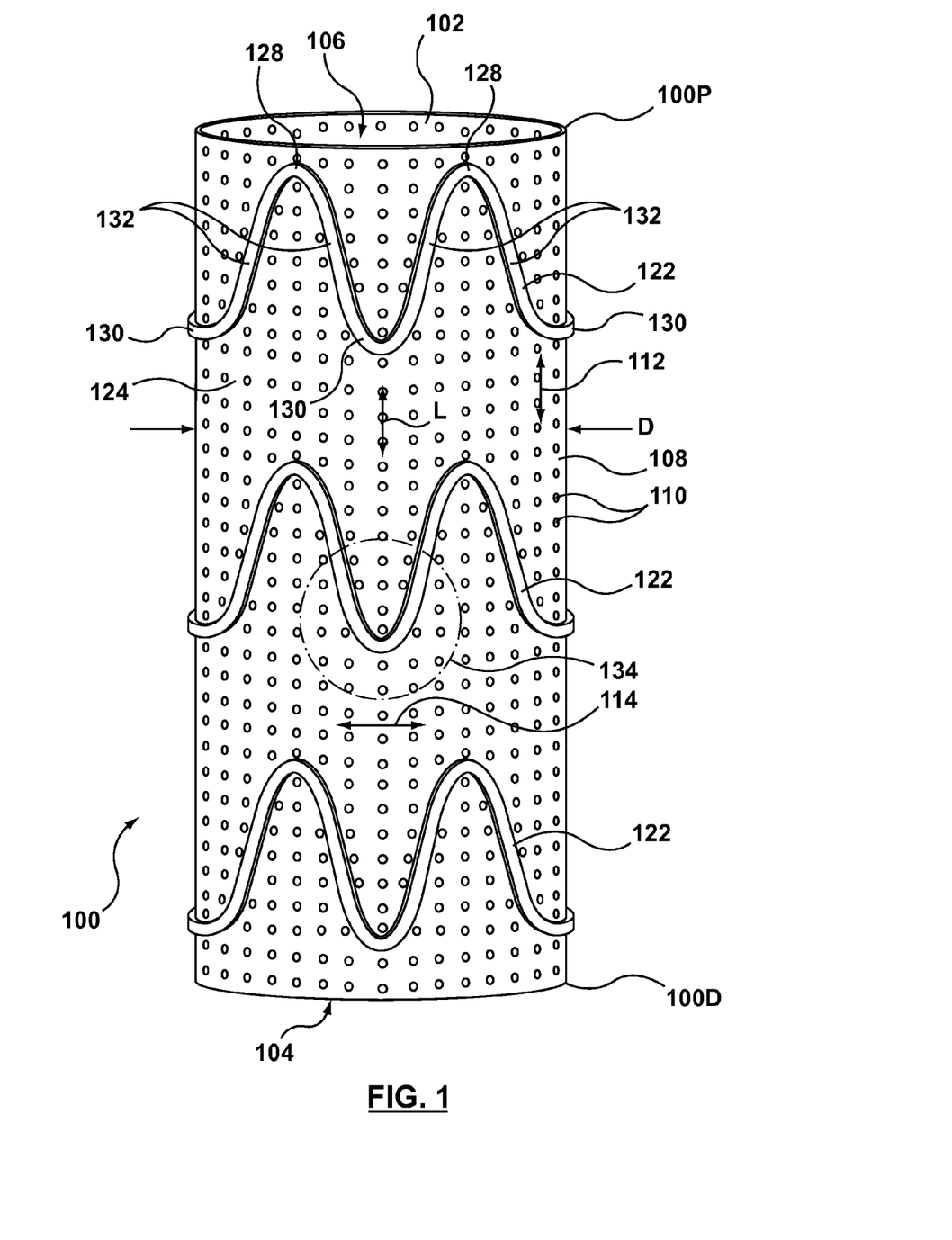
FIG. 1 is a perspective view of an integrated mesh high metal to vessel ratio stent in its final configuration in accordance with one embodiment.
Figure 2:
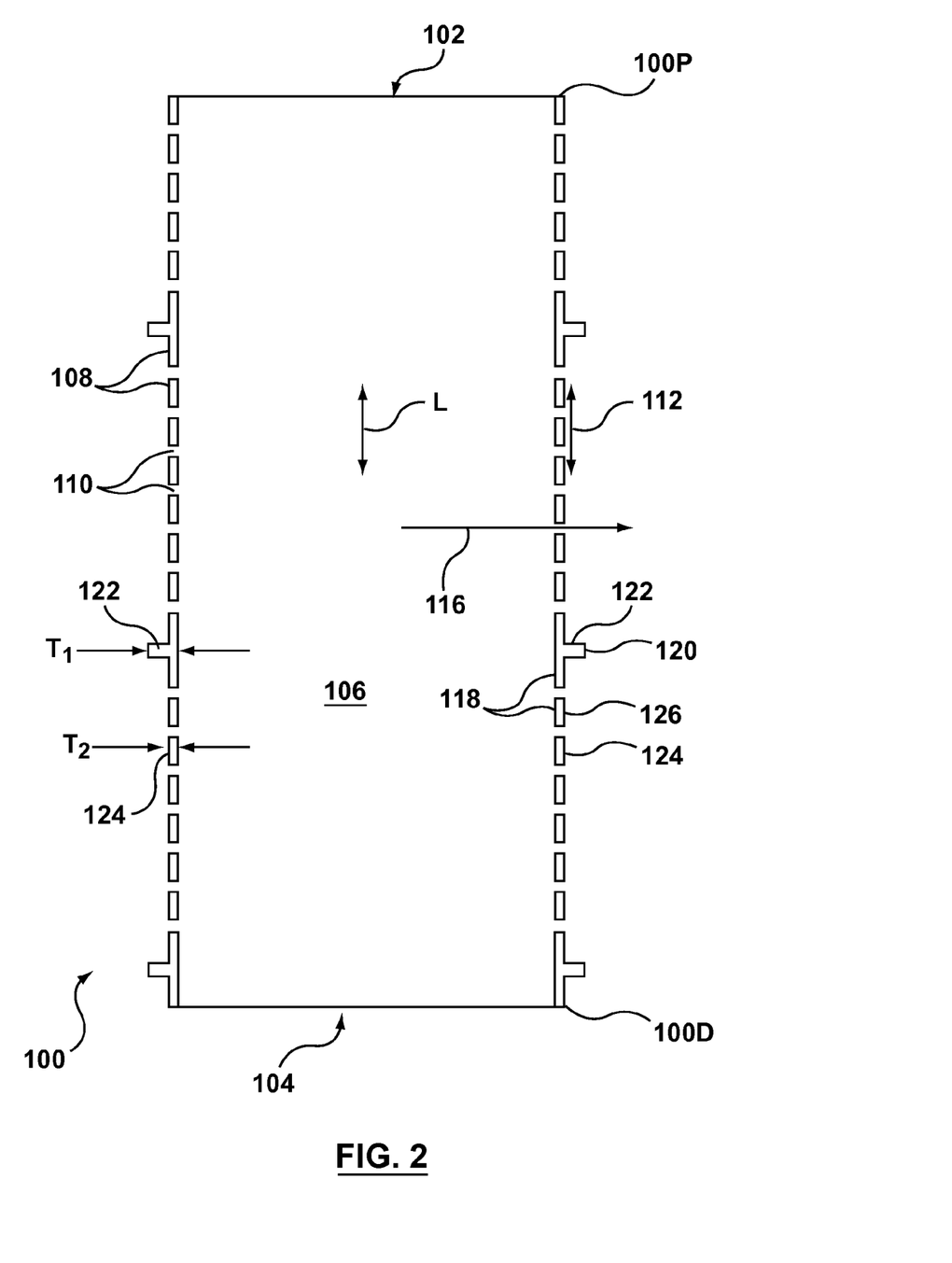
FIG. 2 is a cross-sectional view of the integrated mesh high metal to vessel ratio stent of FIG. 1.

Now in more detail, FIG. 1 is a perspective view of an integrated mesh high metal to vessel ratio stent 100, e.g., an abdominal aortic stent, in its final configuration in accordance with one embodiment. FIG. 2 is a cross-sectional view of integrated mesh high metal to vessel ratio stent 100 of FIG. 1. Integrated mesh high metal to vessel ratio stent 100 is sometimes called an endoluminal flow disrupting device.

Referring now to FIGS. 1 and 2 together, integrated mesh high metal to vessel ratio stent 100 includes a proximal main opening 102 at a proximal end 100P of integrated mesh high metal to vessel ratio stent 100 and a distal main opening 104 at a distal end 100D of integrated mesh high metal to vessel ratio stent 100.

As used herein, the proximal end of a prosthesis such as integrated mesh high metal to vessel ratio stent 100 is the end closest to the heart via the path of blood flow whereas the distal end is the end furthest away from the heart during deployment. In contrast and of note, the distal end of the delivery system is usually identified to the end that is farthest from the operator (handle) while the proximal end of the delivery system is the end nearest the operator (handle).

For purposes of clarity of discussion, as used herein, the distal end of the delivery system is the end that is farthest from the operator (the end furthest from the handle) while the distal end of the prosthesis is the end nearest the operator (the end nearest the handle), i.e., the distal end of the delivery system and the proximal end of the prosthesis are the ends furthest from the handle while the proximal end of the delivery system and the distal end of the prosthesis are the ends nearest the handle. However, those of skill in the art will understand that depending upon the access location, the prosthesis and delivery system description may be consistent or opposite in actual usage.

Integrated mesh high metal to vessel ratio stent 100 is cylindrical and includes a longitudinal axis L. A main lumen 106 is defined by integrated mesh high metal to vessel ratio stent 100 and extends generally parallel to longitudinal axis L and between proximal main opening 102 and distal main opening 104 of integrated mesh high metal to vessel ratio stent 100.

In accordance with this embodiment, integrated mesh high metal to vessel ratio stent 100 has a substantially uniform diameter D. However, in other embodiments, integrated mesh high metal to vessel ratio stent 100 has a non-uniform diameter.

Integrated mesh high metal to vessel ratio stent 100 is a semi-permeable barrier made of patterned material 108, e.g., is an etched and laser perforated tube. Integrated mesh high metal to vessel ratio stent 100 includes patterned material 108 and a plurality of holes 110 through which fluid, e.g., blood, can pass. Generally, integrated mesh high metal to vessel ratio stent 100 is permeable, sometimes called porous, to fluid, i.e., fluid can pass through integrated mesh high metal to vessel ratio stent 100 and more particularly, through holes 110. This allows fluid, e.g., blood, to pass through integrated mesh high metal to vessel ratio stent 100 and nourish, e.g., with oxygen and nutrients, the covered vessel wall. In this manner, hypoxia of the covered vessel wall is avoided. Further, integrated mesh high metal to vessel ratio stent 100 is permeable to tissue ingrowth.

Longitudinal direction 112 is the direction along integrated mesh high metal to vessel ratio stent 100 parallel to longitudinal axis L. Circumferential direction 114 is the direction along the circumference of integrated mesh high metal to vessel ratio stent 100 in plane perpendicular to longitudinal axis L of integrated mesh high metal to vessel ratio stent 100. Radial direction 116 is along a radius extending from longitudinal axis L in plane perpendicular to longitudinal axis L of integrated mesh high metal to vessel ratio stent 100.

Generally, there are a plurality, e.g., three or more, of holes 110 arranged in both longitudinal direction 112 as well as circumferential direction 114.

The ratio of material 108 per unit area of integrated mesh high metal to vessel ratio stent 100 is high, e.g., greater than or equal 30%. This ratio is sometimes called the metal to vessel ratio (or metal to artery ratio) as it defines the percent of the vessel covered with material 108 per unit area of the vessel. Stated another way, the percentage of integrated mesh high metal to vessel ratio stent 100 formed by material 108 is high, e.g., greater than or equal to 30%, and the percentage of integrated mesh high metal to vessel ratio stent 100 formed of holes 110 is low, e.g., less than or equal to 70%.

Generally, the metal to vessel ratio is defined as the area occupied by material 108 of integrated mesh high metal to vessel ratio stent 100 for a unit area of integrated mesh high metal to vessel ratio stent 100 when in the final configuration. To illustrate, for an X square centimeter (cm$^2$) area of integrated mesh high metal to vessel ratio stent 100, Y percent is formed of material 108 whereas Z percent is formed of holes 110, where Y+Z=100. Continuing with this example, Y is the metal to vessel ratio expressed as percent.

To give a specific example for a 40% metal to vessel ratio, for a 1.0 square centimeter area of integrated mesh high metal to vessel ratio stent 100, 0.4 square centimeters would be covered by material 108 whereas 0.6 square centimeters would be covered by holes 110. The metal to vessel ratio can be expressed as a fraction, e.g., 0.4 for this example, or as a percentage, e.g., 40% for this example. To convert, the fraction is multiplied by 100 to obtain the percentage.

Although a fixed metal to vessel ratio is set forth, in other embodiments, the metal to vessel ratio of integrated mesh high metal to vessel ratio stent 100 varies in the longitudinal direction 112 and/or in the circumferential direction 114 along integrated mesh high metal to vessel ratio stent 100.

As set forth above, the metal to vessel ratio is defined when integrated mesh high metal to vessel ratio stent 100 is in the final configuration. Integrated mesh high metal to vessel ratio stent 100 is in the final configuration when in its final unconstrained expanded state, sometimes called at nominal deployment. More particularly, when the diameter of integrated mesh high metal to vessel ratio stent 100 is approximately equal, e.g., 10% to 20% oversized, to the diameter of the vessel in which integrated mesh high metal to vessel ratio stent 100 is being deployed and integrated mesh high metal to vessel ratio stent 100 is at its natural unconstrained length at this diameter, integrated mesh high metal to vessel ratio stent 100 is in its final state. Generally, once deployed within the vessel at its natural unconstrained length as discussed below, integrated mesh high metal to vessel ratio stent 100 is in the final configuration.

The final configuration should be contrasted to the constrained configuration of integrated mesh high metal to vessel ratio stent 100. Integrated mesh high metal to vessel ratio stent 100 is in a constrained configuration when integrated mesh high metal to vessel ratio stent 100 is constrained to a reduced diameter, e.g., within a delivery sheath. Further, integrated mesh high metal to vessel ratio stent 100 is in a constrained configuration when integrated mesh high metal to vessel ratio stent 100 is constrained to a reduced or expanded length, e.g., by longitudinally compressing or expanding integrated mesh high metal to vessel ratio stent 100. When in the constrained configuration, either in length, diameter, or both, holes 110 are collapsed resulting in a much higher metal to vessel ratio for integrated mesh high metal to vessel ratio stent 100 than when integrated mesh high metal to vessel ratio stent 100 and is in its final configuration.

As discussed further below, e.g., in reference to FIGS. 14-17, the metal to vessel ratio of integrated mesh high metal to vessel ratio stent 100 is sufficiently high to encourage tissue ingrowth around integrated mesh high metal to vessel ratio stent 100. However, the metal to vessel ratio of integrated mesh high metal to vessel ratio stent 100 is sufficiently low to ensure adequate perfusion of branch vessel(s) through integrated mesh high metal to vessel ratio stent 100.

Generally, the metal to vessel ratio of integrated mesh high metal to vessel ratio stent 100 is within the range of 30 percent to 80 percent (30-80%), more suitably within the range of 35 percent to 60 percent (35-60%). In one particular embodiment, the metal to vessel ratio is 40 percent (40%).

In one embodiment, integrated mesh high metal to vessel ratio stent 100 is formed of balloon expandable and/or self-expanding metal, e.g., e.g., formed of Nitinol or stainless steel. In one embodiment, integrated mesh high metal to vessel ratio stent 100 is an etched laser perforated formed stent. For example, a cylindrical tube of metal, e.g., Nitinol, is etched and drilled with a laser to form holes 110 therein thus forming integrated mesh high metal to vessel ratio stent 100 as discussed further below in reference to FIGS. 9-13. The cylindrical tube of metal can be formed from a metal sheet that is bent and welded in one embodiment.

As illustrated in FIG. 2, integrated mesh high metal to vessel ratio stent 100 has a first thickness T1, e.g., equal to the thickness of the cylindrical tube from which integrated mesh high metal to vessel ratio stent 100 is formed. Thickness T1 is the distance between an inner cylindrical surface 118 and the outer surfaces 120 of serpentine rings 122 of integrated mesh high metal to vessel ratio stent 100.

Integrated mesh high metal to vessel ratio stent 100 also has a second thickness T2, e.g., equal to the thickness of an integrated mesh 124 of integrated mesh high metal to vessel ratio stent 100. Thickness T2 is the distance between inner cylindrical surface 118 and an outer cylindrical surface 126 of integrated mesh 124 of integrated mesh high metal to vessel ratio stent 100. Thickness T2 is less than thickness T1.

Integrated mesh high metal to vessel ratio stent 100 includes a plurality of serpentine rings 122 connected together by integrated mesh 124. In accordance with this embodiment, integrated mesh high metal to vessel ratio stent 100 includes three serpentine rings 122, however, in other embodiments, integrated mesh high metal to vessel ratio stent 100 includes more or less than three serpentine rings 122.

Serpentine rings 122 include a zigzag pattern, sometimes called a sinusoidal or an alternating repeating pattern. More particularly, each serpentine ring 122 includes a repeating pattern of proximal apexes 128 and distal apexes 130 connected by struts 132. Proximal apexes 128 and distal apexes 130 are sometimes called peaks and valleys, respectively, or crowns.

Integrated mesh 124 is a thin walled cylinder having holes 110 formed therein.

Figure 3:
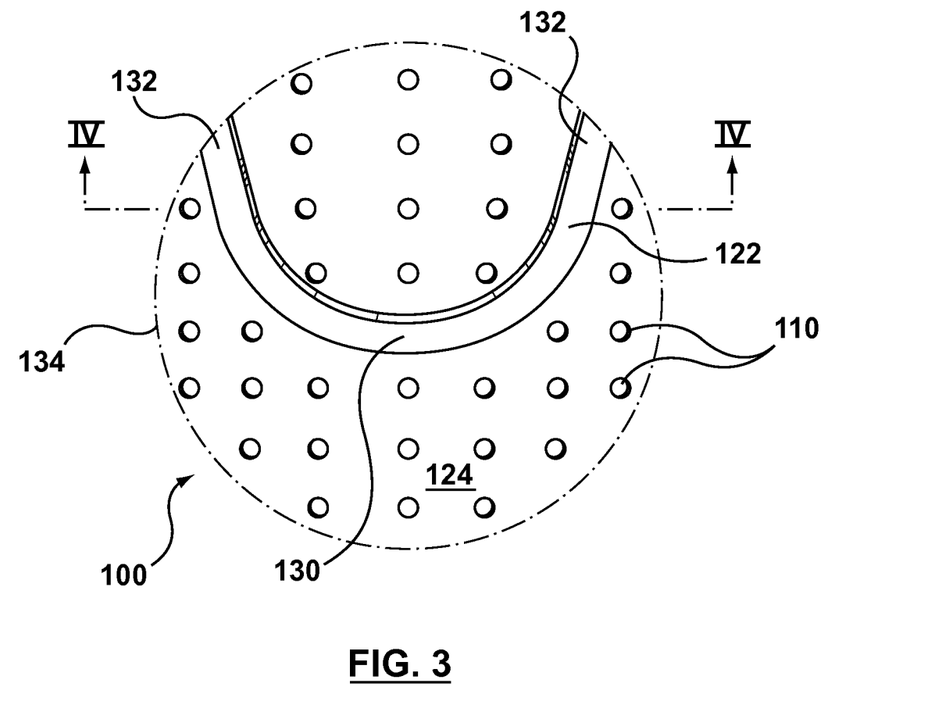
FIG. 3 is an enlarged plan view of a region of the integrated mesh high metal to vessel ratio stent of FIG. 1 in its final configuration in accordance with one embodiment.
Figure 4:
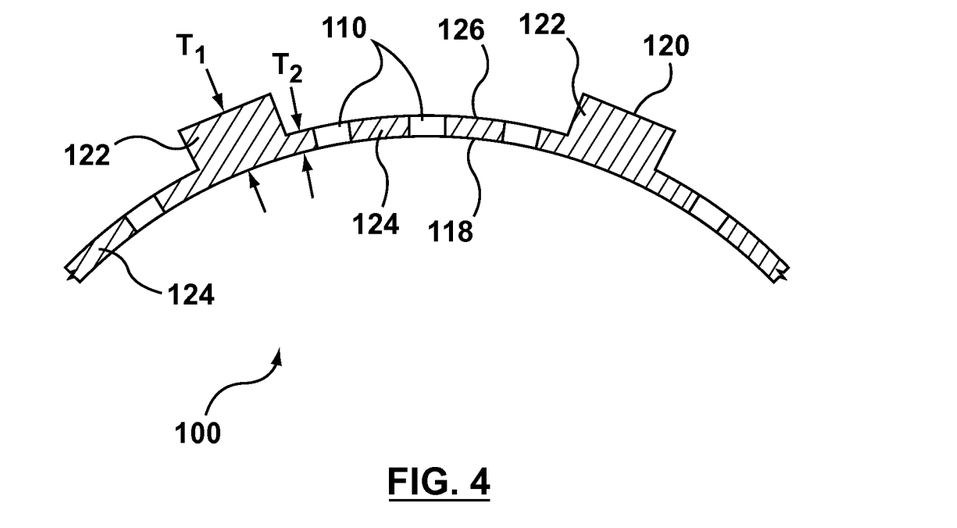
FIG. 4 is a cross-sectional view of the integrated mesh high metal to vessel ratio stent of FIG. 3 along the line IV-IV in accordance with one embodiment.

FIG. 3 is an enlarged plan view of the region 134 of integrated mesh high metal to vessel ratio stent 100 of FIG. 1 in its final configuration in accordance with one embodiment. FIG. 4 is a cross-sectional view of integrated mesh high metal to vessel ratio stent 100 of FIG. 3 along the line IV-IV in accordance with one embodiment.

Referring now to FIGS. 1-4 together, both serpentine rings 122 and integrated mesh 124 have a common inner cylindrical surface 118. Serpentine rings 122 protrude radially outward in radial direction 116 with thickness T1. Integrated mesh 124 is a cylindrical tube having inner cylindrical surface 118 and outer cylindrical surface 126 with thickness T2 between surfaces 118, 126.

Serpentine rings 122, sometimes called stents, provide structural support for integrated mesh high metal to vessel ratio stent 100. Integrated mesh 124 having holes 110 formed therein provides a high metal to vessel ratio for integrated mesh high metal to vessel ratio stent 100.

Figure 5:
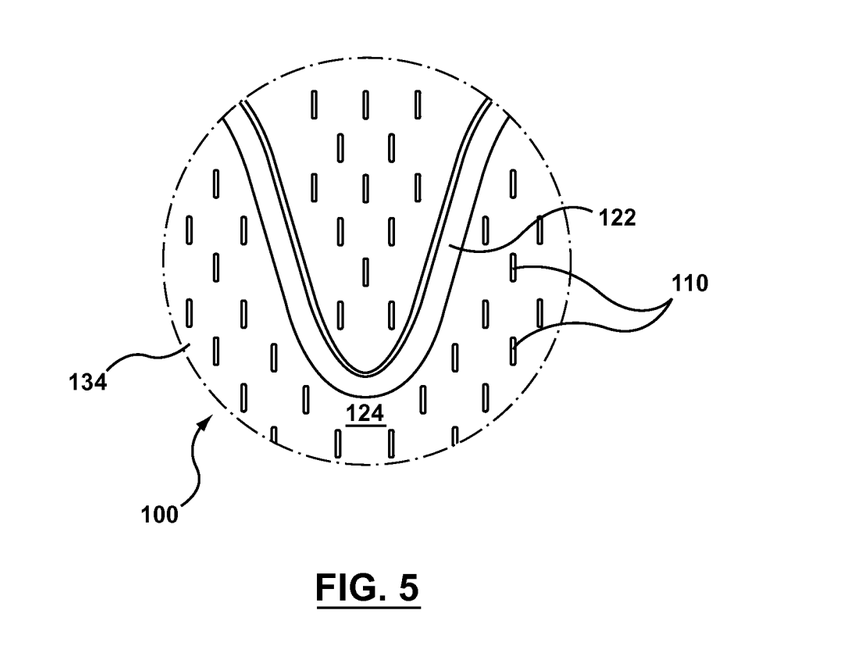
FIG. 5 is an enlarged plan view of the region of the integrated mesh high metal to vessel ratio stent of FIG. 3 in its constrained configuration in accordance with one embodiment.

FIG. 5 is an enlarged plan view of the region 134 of integrated mesh high metal to vessel ratio stent 100 of FIG. 3 in its constrained configuration in accordance with one embodiment. FIG. 5 corresponds to the view of FIG. 3, however, in FIG. 5, integrated mesh high metal to vessel ratio stent 100 is in the constrained, e.g., radially collapsed, configuration, whereas in FIG. 3, integrated mesh high metal to vessel ratio stent 100 is in the final, e.g., radially expanded, configuration.

As illustrated in FIG. 5, when in the constrained configuration, holes 110 are collapsed. This allows integrated mesh high metal to vessel ratio stent 100 to be radially collapsed to an extremely small diameter.

Figure 6:
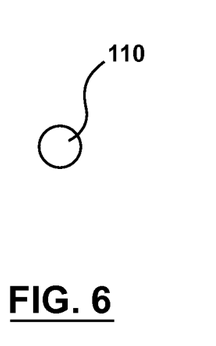
FIG. 6 is an enlarged plan view of a hole of the integrated mesh high metal to vessel ratio stent of FIG. 1-2 in accordance with one embodiment.

FIG. 6 is an enlarged plan view of a hole 110 of integrated mesh high metal to vessel ratio stent 100 of FIG. 1-2 in accordance with one embodiment. In accordance with this embodiment, hole 110 is a circular hole, e.g., formed by laser drilling.

Figure 7:
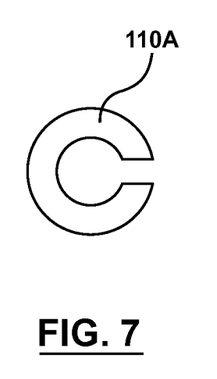
FIGS. 7, 8 are enlarged plan views of a hole of the integrated mesh high metal to vessel ratio stent of FIG. 1-2 in accordance with various embodiments.

FIG. 7 is an enlarged plan view of a hole 110A of integrated mesh high metal to vessel ratio stent 100 of FIG. 1-2 in accordance with another embodiment. In accordance with this embodiment, hole 110A is a partial annulus, sometimes called a C-shaped hole. In one embodiment, hole 110A is formed by moving a laser in a partial circular path.

Figure 8:
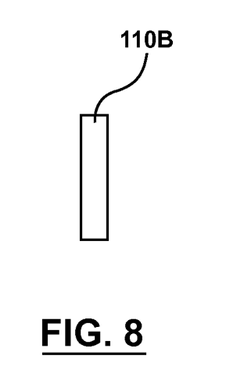

FIG. 8 is an enlarged plan view of a hole 110B of integrated mesh high metal to vessel ratio stent 100 of FIG. 1-2 in accordance with another embodiment. In accordance with this embodiment, hole 110B is linear slot. In one embodiment, hole 110B is formed by moving a laser in a straight path. In accordance with this embodiment, hole 110B can be oriented with its length in longitudinal direction 112, in circumferential direction 114, or in any direction between.

Further, in one embodiment, integrated mesh high metal to vessel ratio stent 100 is formed with a combination, e.g., on or more, of holes 110, 110A, 110B of FIGS. 6, 7, 8, respectively.

Figure 9:
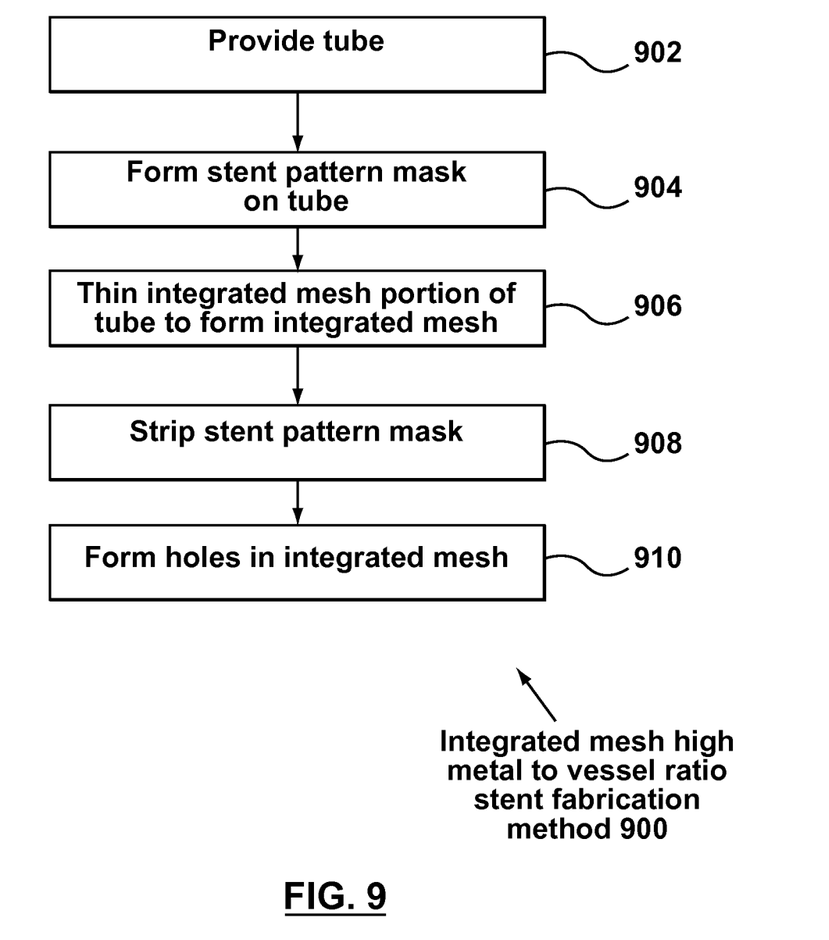
FIG. 9 is a block diagram of an integrated mesh high metal to vessel ratio stent fabrication method of forming the integrated mesh high metal to vessel ratio stent of FIGS. 1-2 in accordance with one embodiment.
Figure 10:
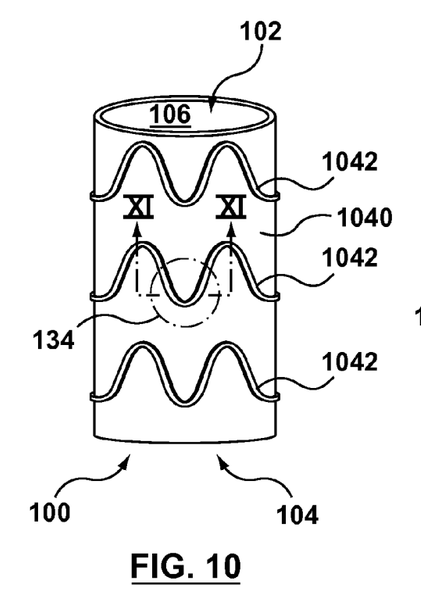
FIG. 10 is a perspective view of the integrated mesh high metal to vessel ratio stent of FIGS. 1-2 during fabrication in accordance with one embodiment.
Figure 11:
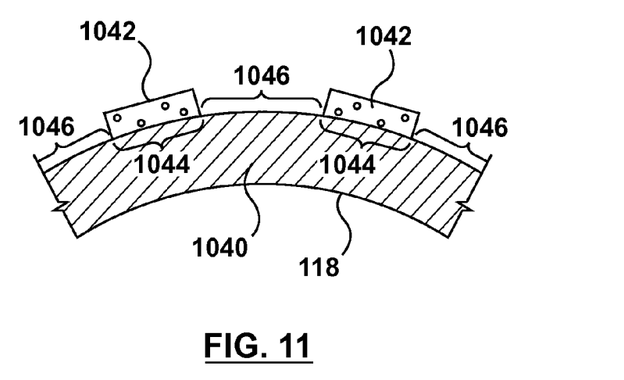
FIG. 11 is a cross-section view of a region of the integrated mesh high metal to vessel ratio stent of FIG. 10 along the line XI-XI in accordance with one embodiment.

FIG. 9 is a block diagram of an integrated mesh high metal to vessel ratio stent fabrication method 900 of forming integrated mesh high metal to vessel ratio stent 100 of FIGS. 1-2 in accordance with one embodiment. FIG. 10 is a perspective view of integrated mesh high metal to vessel ratio stent 100 of FIGS. 1-2 during fabrication in accordance with one embodiment. FIG. 11 is a cross-section view of region 134 of integrated mesh high metal to vessel ratio stent 100 of FIG. 10 along the line XI-XI in accordance with one embodiment.

Referring now to FIGS. 9, 10, and 11 together, in a provide tube operation 902, a tube 1040 is provided. In one embodiment, tube 1040 is formed of Nitinol (NiTi) although is formed of other materials in other embodiment. Tube 1040 has proximal main opening 102, distal main opening 104, and main lumen 106 extending therebetween.

From provide tube operation 902, flow moves to a form stent pattern mask on tube operation 904. In form stent pattern mask on tube operation 904, a stent pattern mask 1042 is formed on tube 1040. Stent pattern mask 1042 has the pattern of serpentine rings 122 to be formed as discussed below. Stent pattern mask 1042 covers and protects serpentine ring portions 1044 of tube 1040 while exposing integrated mesh portion 1046 of tube 1040.

Figure 12:
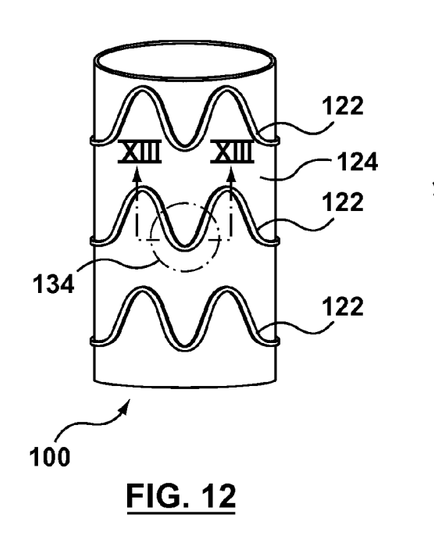
FIG. 12 is a perspective view of the integrated mesh high metal to vessel ratio stent of FIG. 10 at a later stage during fabrication in accordance with one embodiment.
Figure 13:
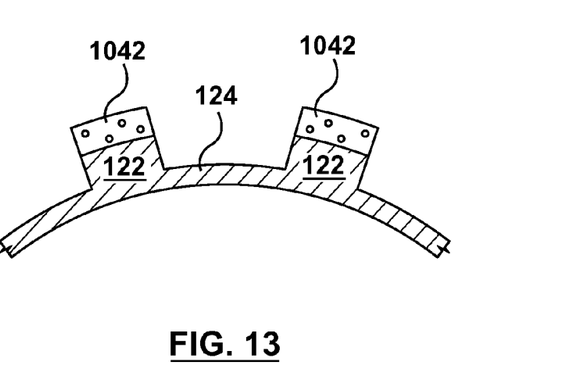
FIG. 13 is a cross-section view of the region of the integrated mesh high metal to vessel ratio stent of FIG. 12 along the line XIII-XIII in accordance with one embodiment.

FIG. 12 is a perspective view of integrated mesh high metal to vessel ratio stent 100 of FIG. 10 at a later stage during fabrication in accordance with one embodiment. FIG. 13 is a cross-section view of region 134 of integrated mesh high metal to vessel ratio stent 100 of FIG. 12 along the line XIII-XIII in accordance with one embodiment.

Referring now to FIGS. 9-13 together, from form stent pattern mask on tube operation 904, flow moves to a thin integrated mesh portion of tube to form integrated mesh operation 906. In thin integrated mesh portion of tube to form integrated mesh operation 906, integrated mesh portion 1046 of tube 1040 is thinned, e.g., by etching, to form integrated mesh 124 (absent holes 110). More particularly, using stent pattern mask 1042 as an etch mask, integrated mesh portion 1046 of tube 1040 is thinned by etching to form integrated mesh 124.

Stent pattern mask 1042 protects serpentine ring portion 1044 from etching. Serpentine ring portion 1044 thus forms serpentine rings 122.

In one embodiment, inner cylindrical surface 118 of tube 1040 is also masked to prevent etching thereof although can be unmasked and etched.

From thin integrated mesh portion of tube to form integrated mesh operation 906, flow moves to a strip stent pattern mask operation 908. In strip stent pattern mask operation 908, stent pattern mask 1042 is stripped, i.e., removed.

From strip stent pattern mask operation 908, flow moves to a form holes in integrated mesh operation 910. In form holes in integrated mesh operation 910, holes 110 are formed in integrated mesh 124. Holes 110 are formed using laser drilling, selective etching, mechanical drilling, or using other hole formation techniques. After performance of form holes in integrated mesh operation 910, integrated mesh high metal to vessel ratio stent 100 as illustrated in FIGS. 1-2 is formed.

Figure 14:
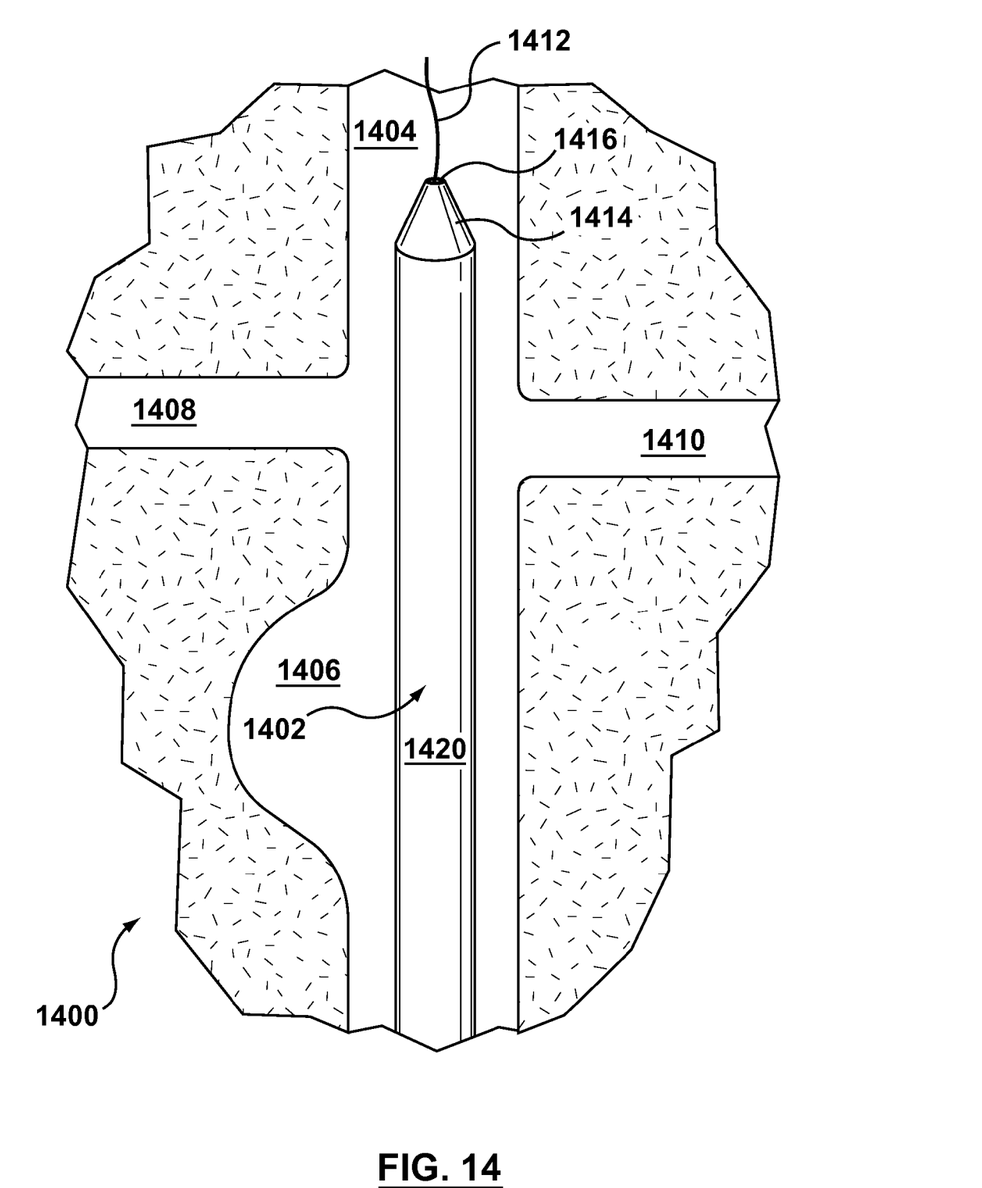
FIG. 14 is a cross-sectional view of a vessel assembly including a delivery system including the integrated mesh high metal to vessel ratio stent of FIGS. 1 and 2 in accordance with one embodiment.
Figure 15:
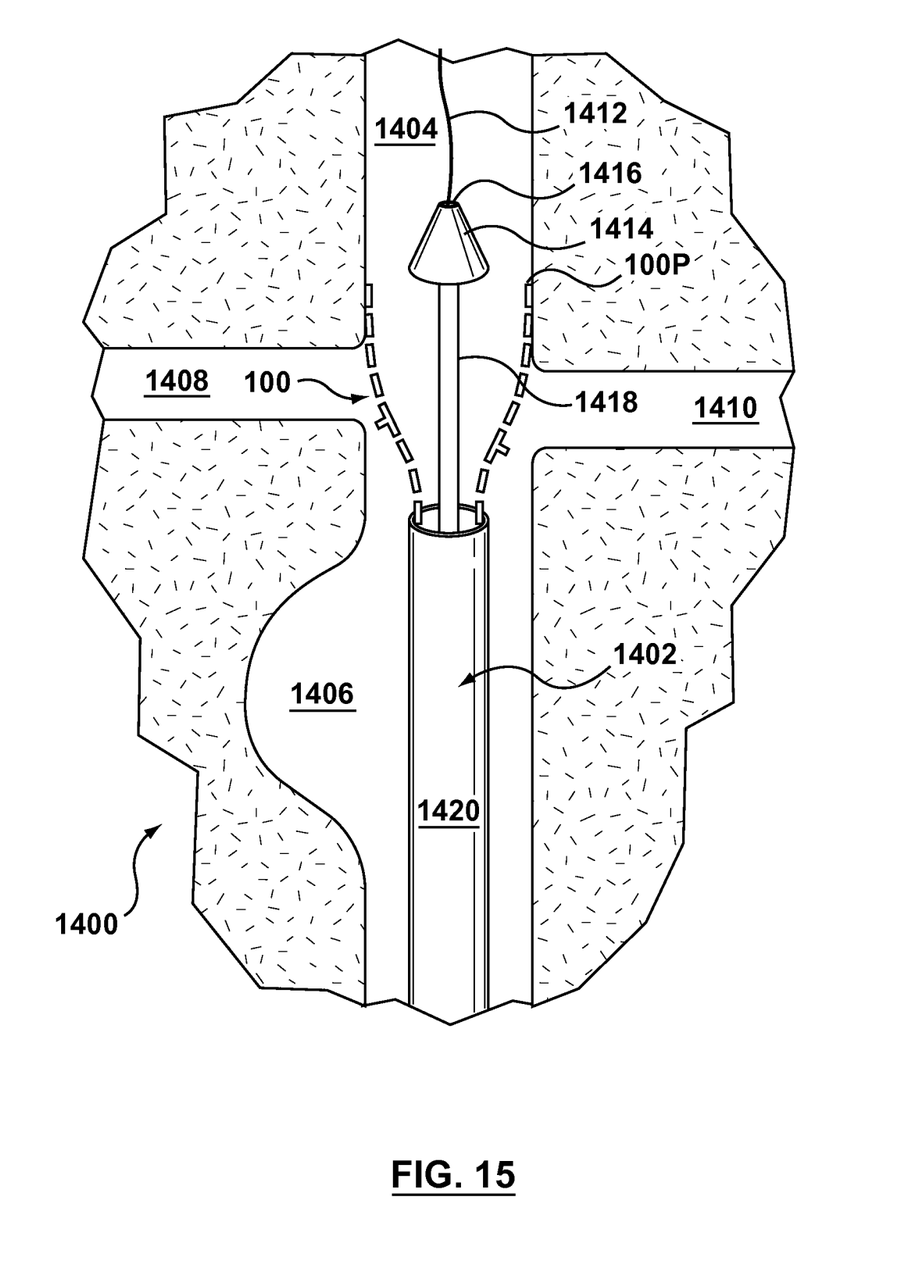
FIG. 15 is a cross-sectional view of the vessel assembly including the delivery system at a later stage of deploying the integrated mesh high metal to vessel ratio stent of FIGS. 1 and 2 in accordance with one embodiment.

FIG. 14 is a cross-sectional view of a vessel assembly 1400 including a delivery system 1402 including integrated mesh high metal to vessel ratio stent 100 of FIGS. 1 and 2 in accordance with one embodiment. FIG. 15 is a cross-sectional view of vessel assembly 1400 including delivery system 1402 at a later stage of deploying integrated mesh high metal to vessel ratio stent 100 of FIGS. 1 and 2 in accordance with one embodiment.

Referring now to FIGS. 14 and 15 together, a main vessel 1404, e.g., the aorta, includes an aneurysm 1406. Integrated mesh high metal to vessel ratio stent 100, sometimes called a prosthesis, is deployed into main vessel 1404 to exclude aneurysm 1406 using delivery system 1402.

Emanating from main vessel 1404 is a first branch vessel 1408 and a second branch vessel 1410, sometimes called visceral branches of the abdominal aorta. The location of branch vessels 1408, 1410 vary from patient to patient. Examples of branch vessels 1408, 1410 include the renal arteries (RA), the superior mesenteric artery (SMA), the brachiocephalic artery, the left subclavian artery, the left common carotid, the celiac trunk, and the hypogastric artery.

Delivery system 1402 is advanced to the location of aneurysm 1406, e.g., over a guidewire 1412, for example as illustrated in FIG. 14. Delivery system 1402 includes a tapered tip 1414 that is flexible and able to provide trackability in tight and tortuous vessels. Tapered tip 1414 includes a lumen 1416 allowing for passage of guidewire 1412 in accordance with this embodiment. In one embodiment, delivery system 1402 includes radiopaque marker(s) that allow visualization of delivery system 1402.

To deploy integrated mesh high metal to vessel ratio stent 100, an inner member 1418 of delivery system 1402 including tapered tip 1414 mounted thereon is held stationary while an outer sheath 1420 of delivery system 1402 is withdrawn, for example, as illustrated in FIG. 15. Integrated mesh high metal to vessel ratio stent 100 is radially constrained by outer sheath 1420 around inner member 1418. Inner member 1418 includes a stent stop or other features to prevent integrated mesh high metal to vessel ratio stent 100 from moving back as outer sheath 1420 is withdrawn.

As outer sheath 1420 is withdrawn, integrated mesh high metal to vessel ratio stent 100 is gradually exposed from proximal end 100P to distal end 100D of integrated mesh high metal to vessel ratio stent 100. The exposed portion of integrated mesh high metal to vessel ratio stent 100 radially expands to be in conforming surface contact with main vessel 1404. More particularly, integrated mesh high metal to vessel ratio stent 100 opposes the walls of main vessel 1404 thus securing integrated mesh high metal to vessel ratio stent 100 in place.

In one embodiment, integrated mesh high metal to vessel ratio stent 100 is self-expanding and thus self expands upon being released from outer sheath 1420. However, in other embodiments, integrated mesh high metal to vessel ratio stent 100 is expanded with a balloon or other expansion device.

Although a particular delivery system 1402 is illustrated in FIGS. 14, 15 and discussed above, in light of this disclosure, those of skill in the art will understand that any one of a number of delivery systems can be used to deploy integrated mesh high metal to vessel ratio stent 100 and the particular delivery system used is not essential to this embodiment.

FIG. 16 is a cross-sectional view of vessel assembly 1400 of FIGS. 14-15 after deployment of integrated mesh high metal to vessel ratio stent 100 of FIGS. 1 and 2 in accordance with one embodiment. Referring now to FIG. 16, integrated mesh high metal to vessel ratio stent 100 is in conforming surface contact with main vessel 1404. Integrated mesh high metal to vessel ratio stent 100 is deployed such that integrated mesh high metal to vessel ratio stent 100 covers, sometimes called jails, ostai (plural of ostium) 1422, 1424 of branch vessels 1408, 1410, respectively.

However, as integrated mesh high metal to vessel ratio stent 100 is permeable, blood flows from main vessel 1404 through integrated mesh high metal to vessel ratio stent 100 and into branch vessels 1408, 1410 thus perfusing branch vessels 1408, 1410. In one embodiment, branch vessels 1408, 1410 are continuously perfused during the entire procedure of deploying integrated mesh high metal to vessel ratio stent 100.

Further, deployment of integrated mesh high metal to vessel ratio stent 100 is relatively simple thus minimizing the complexity and thus risk of deploying integrated mesh high metal to vessel ratio stent 100. More particularly, as the entire integrated mesh high metal to vessel ratio stent 100 is permeable, integrated mesh high metal to vessel ratio stent 100 is deployed without having to rotationally position integrated mesh high metal to vessel ratio stent 100 to be aligned with branch vessels 1408, 1410.

Further, integrated mesh high metal to vessel ratio stent 100 is deployed with fixation and sealing to main vessel 1404 superior to aneurysm 1406, e.g., to healthy tissue of main vessel 1404 adjacent branch vessels 1408, 1410. This minimizes the risk of migration of integrated mesh high metal to vessel ratio stent 100. Further, this allows fixation and sealing of integrated mesh high metal to vessel ratio stent 100 to healthy tissue even when aneurysm 1406 has a short neck, i.e., when the distance between aneurysm 1406 and branch vessels 1408, 1410 is relatively small, as well as when aneurysm 1406 has a highly angulated neck.

Further, integrated mesh high metal to vessel ratio stent 100 covers and excludes aneurysm 1406. More particularly, once integrated mesh high metal to vessel ratio stent 100 is anchored within main vessel 1404, blood flows through main lumen 106 thus excluding aneurysm 1406.

Further, integrated mesh high metal to vessel ratio stent 100 is deployed with fixation and sealing to main vessel 1404 inferior to aneurysm 1406, e.g., to healthy tissue of main vessel 1404. This further facilitates exclusion of aneurysm 1406 while at the same time minimizes the risk of migration of integrated mesh high metal to vessel ratio stent 100.

In other examples, integrated mesh high metal to vessel ratio stent 100 is a bifurcated stent, e.g., integrated mesh high metal to vessel ratio stent 100 is bifurcated to extend into the iliac arteries.

As discussed above, by forming integrated mesh high metal to vessel ratio stent 100 to have a high metal to vessel ratio, branch vessels 1408, 1410 are adequately perfused through integrated mesh high metal to vessel ratio stent 100 while at the same time tissue ingrowth of main vessel 1404 into integrated mesh high metal to vessel ratio stent 100 is encouraged.

FIG. 17 is a cross-sectional view of vessel assembly 1400 of FIG. 16 illustrating tissue 1702 ingrowth into integrated mesh high metal to vessel ratio stent 100. For example, FIG. 17 illustrates ingrowth of tissue 1702 after a period of time, e.g., weeks or months, after the deployment of integrated mesh high metal to vessel ratio stent 100 into main vessel 1404.

Referring now to FIGS. 16 and 17 together, once deployed, integrated mesh high metal to vessel ratio stent 100 includes a fixation region 1704 and a perfusion region 1706. Fixation region 1704 is the region of integrated mesh high metal to vessel ratio stent 100 in direct contact with main vessel 1404. Perfusion region 1706 is the region of integrated mesh high metal to vessel ratio stent 100 covering ostium 1422 of branch vessel 1408 and covering ostium 1424 of branch vessel 1410.

After deployment of integrated mesh high metal to vessel ratio stent 100, tissue 1702 of main vessel 1404 grows through holes 110 of fixation region 1704 of integrated mesh high metal to vessel ratio stent 100. Tissue 1702 encases, sometimes called encloses or encapsulates, material 108 of fixation region 1704 of integrated mesh high metal to vessel ratio stent 100.

This ingrowth of tissue 1702 provides secure fixation and sealing of integrated mesh high metal to vessel ratio stent 100 to main vessel 1404. By providing secure fixation and sealing of integrated mesh high metal to vessel ratio stent 100 to main vessel 1404, the risk of endoleaks into aneurysm 1406 and migration of integrated mesh high metal to vessel ratio stent 100 is minimized. Further, the ingrowth of tissue 1702 restricts expansion of aneurysm 1406. In one embodiment, aneurysm 1406 is remodeled and essentially eliminated as illustrated in FIG. 17.

Further, as illustrated in FIG. 17, tissue 1702 does not grow over perfusion region 1706 of integrated mesh high metal to vessel ratio stent 100. More particularly, blood flows as indicated by the arrows 1708 through holes 110 of perfusion region 1706 to perfuse branch vessels 1408, 1410. Further, this blood flow prevents tissue overgrowth on perfusion region 1706 thus avoiding occlusion of branch vessels 1408, 1410 and the associated complications.

In one embodiment, to encourage tissue ingrowth, integrated mesh high metal to vessel ratio stent 100 includes a surface treatment. Illustratively, a thin layer of metal is applied, e.g., by sputtering, physical vapor deposition (PVD), plasma enhanced chemical vapor deposition (PECVD), or other application technique, to integrated mesh high metal to vessel ratio stent 100 to encourage tissue ingrowth.

Examples of suitable metals include gold, stainless steel, titanium oxide, and/or copper, or combinations thereof are applied to integrated mesh high metal to vessel ratio stent 100 to encourage tissue ingrowth.

In another embodiment, the surface treatment includes roughening the surface of integrated mesh high metal to vessel ratio stent 100 to encourage tissue ingrowth. For example, the surface is roughened to have a roughness average (RA) of greater than 1.0 micron ($\mu$m). The surface can be roughened by plasma etching, laser etching, sandblasting, a selective etch to preferentially etch one component of integrated mesh high metal to vessel ratio stent 100 over another, or other surface roughening technique.

In yet another embodiment, the surface treatment includes a growth factor applied to integrated mesh high metal to vessel ratio stent 100 to enhance tissue ingrowth into integrated mesh high metal to vessel ratio stent 100. Examples of growth factors include vascular endothelial growth factor (VEGF), platelet-derived growth factor (PDGF), plated-derived epidermal growth factor (PDEGF), fibroblast growth factors (FGFs), basic fibroblast growth factor (bFGF), transforming growth factor-beta (TGF-.beta.), platelet-derived angiogenesis growth factor (PDAF) and autologous platelet gel (APG).

Another example of growth factors include bioactive materials, e.g., a bioactive compound, drug, therapeutic agent or composition having a biological effect in an animal. Bioactive materials include small molecules, peptides, proteins, hormones, DNA or RNA fragments, genes, cells, genetically-modified cells, cell growth promoting compositions, inhibitors of matrix metalloproteinase, fatty acids and autologous platelet gel.

Although treatment of aneurysm 1406 is illustrated in the figures and discussed above, in other embodiments, other vessel defects are treated using devices and methods as described herein. For example, other aortic pathologies such as dissections and penetrating ulcers are treated.

This disclosure provides exemplary embodiments. The scope is not limited by these exemplary embodiments. Numerous variations, whether explicitly provided for by the specification or implied by the specification or not, such as variations in structure, dimension, type of material and manufacturing process may be implemented by one of skill in the art in view of this disclosure.

What is claimed is:

1. A prosthesis comprising:
   serpentine rings; and
   an integrated mesh connecting the serpentine rings, wherein a metal to vessel ratio of the prosthesis when in a final configuration is within the range of 30 percent to 80 percent such as to encourage tissue ingrowth around the prosthesis while ensuring perfusion of a branch vessel through walls the prosthesis.

2. The prosthesis of claim 1 wherein the metal to vessel ratio is within the range of 35 percent to 60 percent.

3. The prosthesis of claim 1 wherein the serpentine rings comprise proximal apexes, distal apexes, and struts connecting the proximal apexes and the distal apexes.

4. The prosthesis of claim 1 wherein the integrated mesh comprises a plurality of holes therein.

5. The prosthesis of claim 4 wherein the holes are circular.

6. The prosthesis of claim 4 wherein the holes are partial annuli.

7. The prosthesis of claim 4 wherein the holes are linear slots.

8. The prosthesis of claim 1 wherein the serpentine rings have a first thickness and the integrated mesh has a second thickness, the first thickness being greater than the second thickness.

9. The prosthesis of claim 1 wherein the integrated mesh comprises a cylinder having holes therein.

10. The prosthesis of claim 1 wherein the serpentine rings and the integrated mesh have a common inner cylindrical surface.

11. The prosthesis of claim 1 further comprising:
    a surface treatment to encourage the tissue ingrowth.

12. The prosthesis of claim 11 wherein the surface treatment comprises a metal.

13. The prosthesis of claim 11 wherein the surface treatment comprises roughening the prosthesis.

14. The prosthesis of claim 11 wherein the surface treatment comprises a growth factor.

* * * * *